US006779384B2

(12) United States Patent
Chun

(10) Patent No.: US 6,779,384 B2
(45) Date of Patent: Aug. 24, 2004

(54) DEVICE AND METHOD FOR MEASURING A DIFFUSION COEFFICIENT OF NANO-PARTICLE FLUID THROUGH HOLLOW-FIBER MICROPORES

(75) Inventor: Myung-Suk Chun, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 10/339,201

(22) Filed: Jan. 8, 2003

(65) Prior Publication Data

US 2004/0093934 A1 May 20, 2004

(30) Foreign Application Priority Data

Nov. 19, 2002 (KR) .................................. 10-2002-71884

(51) Int. Cl.[7] ........................ G01N 13/04; G01N 15/08
(52) U.S. Cl. ......................................... 73/64.47; 73/38
(58) Field of Search ..................... 73/38, 64.47, 64.56, 73/61.73; 210/649, 745, 741, 746; 436/514

(56) References Cited

U.S. PATENT DOCUMENTS

| | | | | |
|---|---|---|---|---|
| 5,513,515 A | * | 5/1996 | Mayer ............................ | 73/38 |
| 5,913,235 A | * | 6/1999 | Silenius et al. ................ | 73/38 |
| 6,076,395 A | * | 6/2000 | Black et al. ................ | 73/64.47 |
| 6,298,713 B1 | * | 10/2001 | Nandu et al. .............. | 73/64.47 |
| 6,387,329 B1 | * | 5/2002 | Lewis et al. ................... | 422/98 |
| 6,463,790 B1 | * | 10/2002 | Chun et al. ..................... | 73/38 |

OTHER PUBLICATIONS

Chemical Engineering Science, vol. 33, No. 11–B, pp 1429–1440 "Hindered Diffusion of Particles Through Small Pores" by Dermot M. Malone and J.L. Anderson.

Industry and Engineering Chemistry Research 1998, vol. 27, pp 866–871 "Pore Size Effects on Diffusion of Polystyrene in Dilute Solution" by I.A. Kathawalla; J. L. Anderson.

Journal of Membrane Science, vol. 47 (1989), pp. 163–182 "Hindered Transport Through Micropores with Adsorbed Polyelectrolytes" by J.T. Kim, J.L., Anderson.

Langmuir 1989, vol. 5, pp 932–938 "Diffusion of Charged Micelles Through Charged Microporous Membranes" by K.A. Johnson, G. B. Westerman–clark: D.O. Shah.

Journal of Colloid and Interface Science, vol. 153, No. 2, pp. 483–492 "Charge Effects on the Diffusion of Polystyrene Sulfonate Through Porous Membranes" by N.P. Lin; W.M. Deen.

American Institute of Chemical Engineers Journal (Jun. 2000), vol. 46, No. 6 "Hindered Diffusion of Dextran and Polyethylene Gylcol in Porous Membranes" by J. Shao; R.E. Baltus.

American Institute of Chemical Engineers Journal (Jul. 2000), vol. 46, No. 7 "Effect of Solute Concentration on Hindered Diffusion in Porous Membranes" by J. Shao; R.E. Baltus.

* cited by examiner

Primary Examiner—Helen Kwok
(74) Attorney, Agent, or Firm—Jones Day

(57) ABSTRACT

A particle diffusion coefficient measuring device is provided with a hollow-fiber including micropores on its surface. The hollow-fiber provides a passage for particle suspension to transport through. The device is also provided with a fluid passage formed outside the hollow-fiber to communicate with the hollow-fiber via the micropores. The fluid passage provides a passage for an electrolyte solution to transport through in such a manner that the electrolyte solution is delivered to flow in the same direction as that of the particle suspension and is discharged from the fluid passage. The device detects a concentration change of the particles in the electrolyte solution discharged out of the fluid passage over a time change and calculates a particle diffusion coefficient by using the concentration change of the particles over the time change.

9 Claims, 6 Drawing Sheets

DEVICE AND METHOD FOR MEASURING A DIFFUSION COEFFICIENT OF NANO-PARTICLE FLUID THROUGH HOLLOW-FIBER MICROPORES

FIELD OF THE INVENTION

The present invention relates to a device and method for measuring a particle diffusion coefficient, and particularly to a device and method for measuring a diffusion coefficient of particles of suspensions, in which colloids, nano-particles, bio-macromolecules, inorganic particles or the like are dispersed, when the particles are transported through micropores of a hollow-fiber.

BACKGROUND OF THE INVENTION

To date, many studies on diffusion of particles through the confined spaces of micropores have been conducted. In most of these known studies dealing with flat type membranes, an electrolyte introduced into a diffusion cell is stirred for promoting the diffusion and then a measurement is performed to detect a change of particle concentration, in order to measure the diffusion coefficient.

The followings are publications related to the particle diffusion through the confined micropores.

In the journal of "Chemical Engineering Science", Volume 33, Issue 11, Dermot M. Malone and John L. Anderson propose a diffusion cell by which the hindered diffusion behavior of latex particles with diameter of 91 nm in a track-etched flat type membrane having well-defined cylindrical micropores of a preset size, can be observed. They also disclose results of the hindered diffusion coefficient according to a change in the ionic concentration (i.e. ionic strength) of potassium chloride electrolyte solution with respect to various micropores having a different size.

Imtiaz A. Kathawalla and John L. Anderson disclose the measurements of hindered diffusion coefficient for the linear flexible chain of polystyrene with dilute concentration (molecular weight: $1.6$–$9.3 \times 10^5$ Daltons) through the micropores of track-etched flat type membrane made of mica, in the journal of "Industry and Engineering Chemistry, Research", Volume 27, Issue 5. This reference proposes a diffusion cell for the flat type membrane, which has a simple configuration and is more efficient in delivering the solutions thereinto, compared to existing units.

Jeenok T. Kim and John L. Anderson describe a study on both the hindered diffusion phenomenon and the hydrodynamic thickness developed near a wall surface of micropores in a situation where the macromolecular dextrans with different molecular weights are transported through the micropores adsorbed with polystyrene sulfonate in the "Journal of Membrane Science", Volume 163, pages 163–182. They used a track-etched flat type membrane made of mica and detected a minute change of the concentration caused by diffusion by employing a fluorescent probe method in which the optical fibers are applied.

In the journal "Langmuir", Volume 5, Issue 4, Keith A. Johnson et al. disclose results of a hindered diffusion coefficient of the micelle measured where the micelle was diffused through the straight cylindrical micropores of flat type membrane made of polycarbonate. They exemplified a case in which the radius of colloidal particles is ten times larger than that of the micropores and the ionic strength of electrolyte solution is low, so as to show that the long-range interaction between colloidal particles and the wall surface of the micropores has a considerable influence on the particle diffusion.

In the "Journal of Colloid and Interface Science", Volume 153, Issue 2, Nelson P. Lin and William M. Deen disclose a study on measurement of a hindered diffusion coefficient of potassium polystyrene sulfonate, which is a polyelectrolyte, with respect to the micropores of flat type membrane. This reference shows that the experimental measurements fairly coincide with the theoretical prediction.

In the "American Institute of Chemical Engineers Journal", Volume 46, Issue 6, Jiahui Shao and Ruth E. Baltus measure the hindered diffusion coefficients of both the dextrans with molecular weights of $1.6$–$6.2 \times 10^5$ Daltons and the polyethylene glycol with a molecular weight of about $11 \times 10^5$ Daltons, through the micropores with sizes of 0.03, 0.05, and 0.1 $\mu$m in a track-etched flat type membrane made of polycarbonate. When the Stokes-Einstein equation is applied with the measurements, the respective theoretical radii were 3.6–5.3 nm for dextran and 3.0 nm for polyethylene glycol. From a comparison between the measurements and the model prediction, they show that, besides the steric exclusion and the electrostatic repulsion, the van der Waals attraction also affects on the hindered diffusion coefficient.

In the "American Institute of Chemical Engineers Journal", Volume 46, Issue 7, Jiahui Shao and Ruth E. Baltus measure a hindered diffusion coefficient of the same solute particles as used in the above described reference, taking concentrations of about 20, 42, and 60 mg/mL through the same membrane as used in the above described reference. They compared the experimental values of the diffusion coefficient depending on an increase of the particle concentration with the model prediction, and analyzed the hindered diffusion behavior in view of the related interaction potential.

All of the above described studies and citations are related to the measurements of hindered diffusion coefficient through the micropores of flat type membranes, however, they cannot really be applied to the micropores of hollow-fiber having a different geometrical configuration from the flat type membrane.

Therefore, there has been a need for developments of a method and device for measuring a diffusion coefficient of particles through the micropores of hollow-fiber.

SUMMARY OF THE INVENTION

It is, therefore, an object of the present invention to provide a device and method for measuring particle diffusion coefficient by flowing both a particle suspension and a electrolyte solution in a "con-current" mode, where the particle suspension flows through an inner space (i.e., tube-side) of a hollow-fiber, while the electrolyte solution flows through an outer space (i.e., shell-side) of the hollow-fiber, thereby measuring the diffusion coefficient through the micropores of the hollow-fiber in a short time with small amount of the feed solution.

The object and other objects, which will become apparent to those skilled in the art, are accomplished with a measuring device of particle diffusion coefficient provided with a hollow-fiber including micropores on its surface. The hollow-fiber provides a passage for a particle suspension to transport through. The device is also provided with a fluid passage formed outside the hollow-fiber to communicate with the hollow-fiber via the micropores. The fluid passage provides a passage for an electrolyte solution to transport through in such a manner that the electrolyte solution is delivered to flow in a same direction as that of the particle suspension and is discharged from the fluid passage. The device detects a concentration change of the particles in the electrolyte solution discharged out of the fluid passage over a time change and calculates a particle diffusion coefficient by using the concentration change of the particles over the time change.

In accordance with one aspect of the present invention, a method of particle diffusion coefficient measurement is provided. The method comprises the steps of (a) flowing a first fluid having particles into the inside of a hollow-fiber and flowing a second fluid into the outside of a hollow-fiber in a same direction as that of the first fluid, the fluid passage communicating with the inside of the hollow-fiber; (b) discharging the second fluid; (c) detecting a change in the particle concentration in the second fluid being discharged out of the fluid passage over the time change; and (d) calculating a diffusion coefficient by using the concentration change of the particles over the time change.

In accordance with another aspect of the present invention, the method described above further comprises the steps of calculating a hindered diffusion coefficient by using the concentration change of the particles over the time change and the particle diffusion coefficient.

BRIEF DESCRIPTION OF DRAWINGS

The above and other objects involving features of the present invention will become more apparent from the following description of the preferred embodiments given in conjunction with the accompanying drawings.

DETAILED DESCRIPTION OF THE PRESENT INVENTION

A preferred embodiment of the present invention will now be described with reference to the accompanying drawings.

Figure 1:
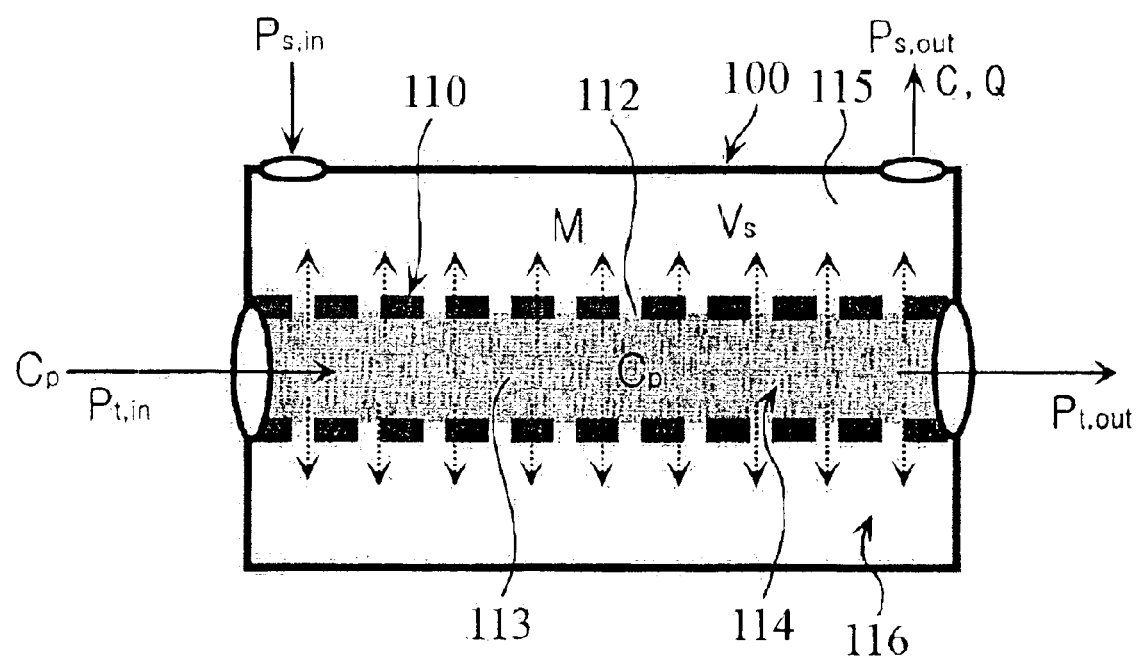
FIG. 1 is a schematic view for illustrating a hindered diffusion phenomenon occurring when suspended particles are transported through micropores of a hollow-fiber.

FIG. 1 is a schematic view to explain a hindered diffusion phenomenon which occurs when the suspended particles are transported through micropores of a hollow-fiber.

Referring to FIG. 1, in order to obtain a diffusion coefficient of particles through the micropores of the hollow-fiber 110, the present invention provides a diffusion cell 100 having therein a hollow-fiber 110 through which a particle suspension 113 flows. In the particle suspension 113, particles are dispersed. Formed outside the hollow-fiber 110 in parallel with the hollow-fiber 110 is an outer space 116 through which an electrolyte solution 115 flows in the same direction as the particle suspension 113.

In the present invention, it needs to minimize undesirable influences by factors other than a natural diffusion such as convection when the particles are diffused into the outer space 116 through the micropores 112 of the hollow-fiber 110, from the inner space 114 of the hollow-fiber 110 mounted within the diffusion cell 100.

For this, the linear velocity of particle suspension 113 flowing through the inner space 114 of the hollow-fiber 110 is maintained at a velocity equals to that of the electrolyte solution 115 flowing through the outer space 116. A proportion of the pressure difference between inlet pressure $P_{s\text{-}in}$ and outlet pressure $P_{s\text{-}out}$ of the electrolyte solution 115, to the pressure difference between inlet pressure $P_{t\text{-}in}$ and outlet pressure $P_{t\text{-}out}$ of the particle suspension is maintained to be constant. Further, the diffusion cell 100 is maintained at a constant temperature.

The inventive device for measuring a diffusion coefficient is configured to measure a fine change in the particle concentration over a time change, where particles are diffused through the micropores 112 of the hollow-fiber 110, under a consideration of such new ideas that have never been tried so far.

The particle suspension 113 is delivered into the inner space 114 of the hollow-fiber 110 at a particle inlet concentration $C_p$, and particles are diffused into the electrolyte solution 115 of the outer space 116 at diffusion rate M through the micropores 112 and are then detected at an outlet of the outer space 116 at a particle outlet concentration C. The electrolyte solution 115 flowing through the outer space 116 of a preset volume $V_s$ is discharged out of the diffusion cell 100 at a constant flow rate Q. The hollow-fiber 110 has an effective contact area A.

In order to obtain the diffusion coefficient of the particles diffused through the micropores 112 of the hollow-fiber 110 in the inventive measuring device, a change in particle concentration (dC/dt) over a change in time (t) is first measured. From this, the diffusion coefficient is calculated with the following mass balance equations, which can be adopted from the previous researches such as either the "Chemical Engineering Science", Volume 33, Issue 11 or "Experimental Study on the Hindered Diffusion of Concentrated Latexes through Track-Etched Membrane Pores" published in the "Journal of Korean Institute of Chemical Engineers", Volume 37, Issue 1, issued on February 1999.

$$V_s \frac{dC}{dt} = M - QC \qquad \text{Equation 1}$$

$$M = KA(C_p - C) \qquad \text{Equation 2}$$

$$\frac{1}{K} = R_m + 2R_e = \frac{L}{\alpha D^p} + \frac{(\pi/2)r_p}{\alpha D_\infty} \qquad \text{Equation 3}$$

Wherein, K is the overall mass transfer coefficient for micropore, $R_m$ a resistance of the micropore with length L, $R_e$ a resistance due to an end effect of the micropore with radius of $r_p$, $\alpha$ a surface porosity, $D^p$ a particle diffusion coefficient in the micropore, and D a particle diffusion coefficient in the bulk, and $C_p \gg C$ is satisfied.

Consequently, the present invention determines the diffusion coefficient by first obtaining data of concentration change of particles according to the time change, and second, using the data and the equations described above.

Once the particle diffusion coefficient through the micropores of the hollow-fiber is determined in this scheme, then a hindered diffusion coefficient can be calculated.

The suspended particles employed in the present invention may be various particles having a size in nanometers order including colloids, bio-macromolecules, other inorganic particles or the like.

Figure 2:
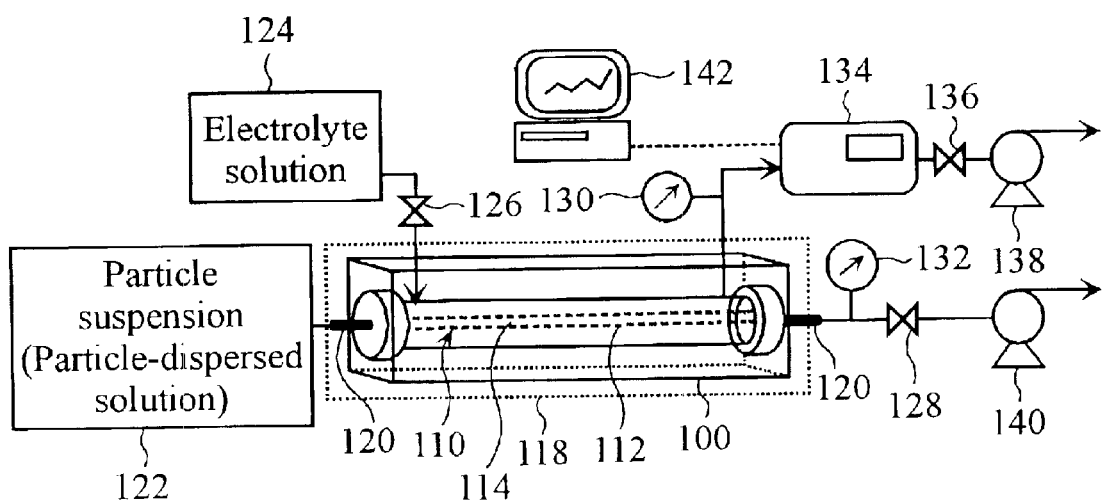
FIG. 2 is a schematic view of a device for measuring a diffusion coefficient of particles through the micropores of the hollow-fiber in accordance with the present invention.

The inventive device for measuring the diffusion coefficient of particles through the micropores of the hollow-fiber will be described with the reference to FIGS. 2, 3a and 3b. The inventive measuring device comprises a diffusion cell 100 containing the hollow-fiber 110.

Figure 3A:
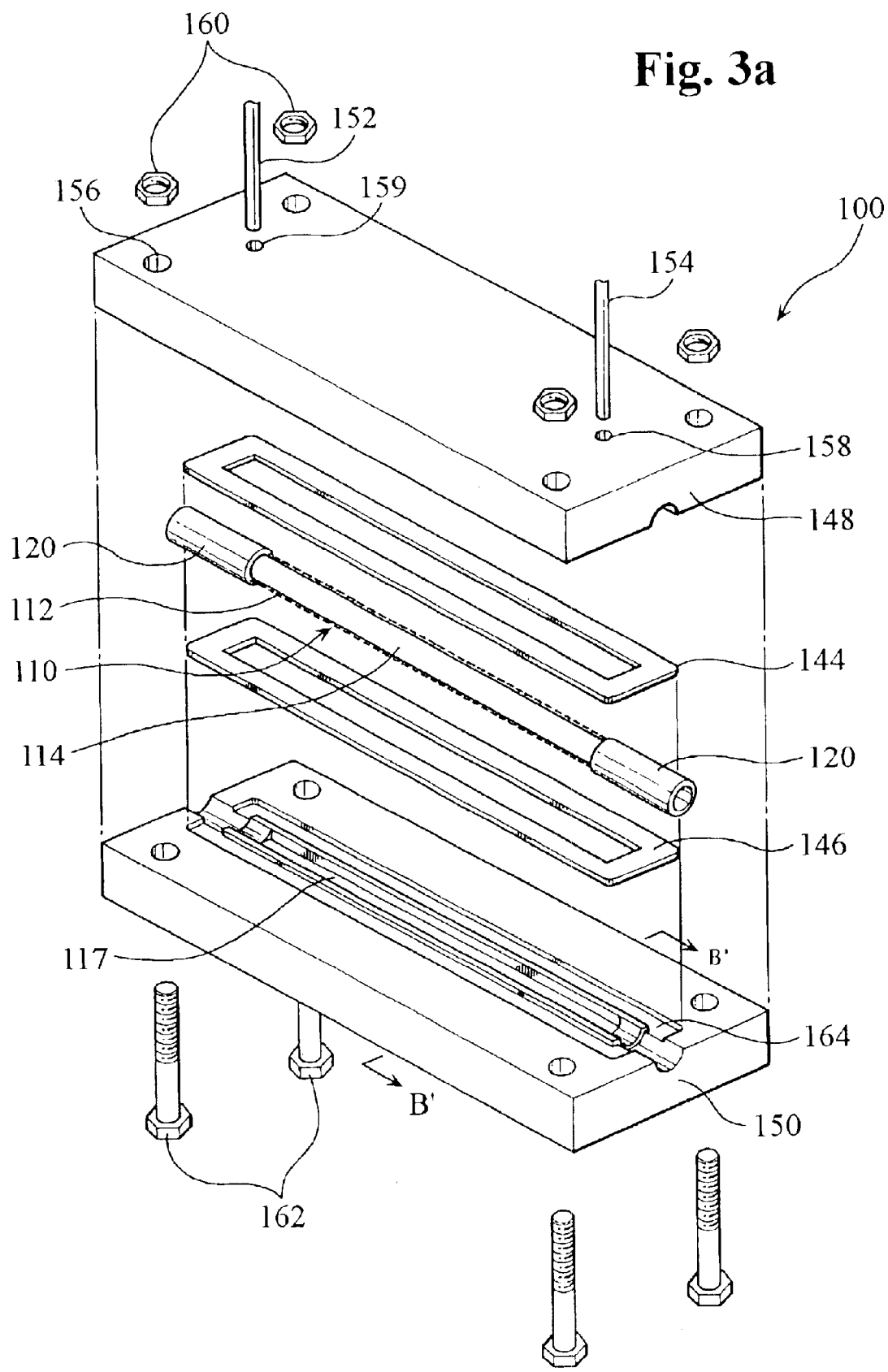
FIG. 3a presents an exploded perspective view of a diffusion cell employed in the inventive device for measuring the diffusion coefficient through the micropores of the hollow-fiber.

FIG. 3a is an exploded perspective view of the diffusion cell 100. Diffusion cell 100 comprises an upper cell 148, a lower cell 150, a pair of sealing members 144, 146, a connection tube 120 connected to the hollow-fiber 110, with a sealing provided therebetween, to communicate with the inner space 114, and a plurality of bolts 162 and nuts 160 coupling the upper cell 148 to the lower cell 150. Both ends of the hollow-fiber 110 are connected to the connection tube 120 by, e.g., potting to fabricate a module.

Figure 3B:
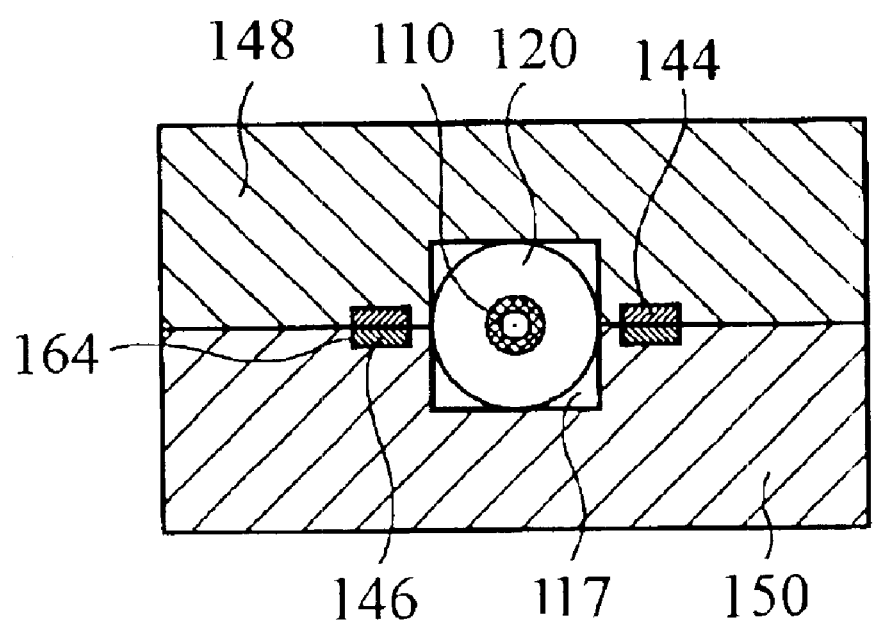
FIG. 3b is a sectional view of the diffusion cell shown in FIG. 3a, when taken along a line B'—B'.

Referring to FIGS. 3a and 3b, both the upper cell and the lower cell 148, 150 have the same dimensions, and are each provided with a first groove 117 forming the outer space 116 through which the hollow-fiber 110 and the connection tube 120 extend and a second groove 164 on which the sealing members 144, 146 are positioned. As shown in FIG. 3b, it is preferable that the first groove 117 be of square shape in its cross-section. The pair of sealing members 144, 146, each has a cutout through a center thereof. When the upper cell 148 is coupled to the lower cell 150, the pair of sealing members 144, 146 each surrounds the portions of the connection tube 120 at both ends, thereby allowing the outer space 116 formed by the first groove 117, to be sealed.

A through hole 159 formed through the upper cell 148, which connects an electrolyte solution reservoir 124 to the outer space 116 and a through hole 158, is also formed through the upper cell, which functions as a passage for the electrolyte solution 115 to be discharged out of the diffusion cell 200.

Returning to FIGS. 2 and 3a/3b, the connection tube 120 through which the particle suspension 113 is delivered, is connected to a particle suspension reservoir 122, while the connection tube 120 on the other side is connected to a suction pump 140 via a pressure gauge 132 and a flow control valve 128. The pressure gauge 132 indicates a minute change in pressure within the inner space 114 of the hollow-fiber 110 and the flow control valve 128 serves to accurately control the flow rate of the particle suspension 113 flowing through the inner space 114.

The outer space 116 communicates with the electrolyte solution reservoir 124 via a connection tube 152 and is connected to a suction pump 138 via a pressure gauge 130, a concentration detector 134 and a flow control valve 136. The pressure gauge 130 indicates a minute change in pressure within the outer space 116 and the flow control valve 136 serves to accurately control the flow rate of the electrolyte solution 115 flowing through the outer space 116. The concentration detector 134 serves to measure the concentration of the particles from the electrolyte solution 115 discharged out of the diffusion cell 100. Although various known concentration detectors may be used in the present invention, a refractive index detector is adopted in the present invention.

When the suction pump 138 is operated, the electrolyte solution 115 is delivered into the outer space 116 from the electrolyte solution reservoir 124. Flow rate of the electrolyte solution 115 flowing through the outer space 116 can be adjusted by control of the flow control valve 136. Similarly, when the suction pump 140 is operated, the particle suspension 113 is delivered into the hollow-fiber 110 from the reservoir 122. The flow control valve 128 can control the flow rate of the particle suspension 113.

Although both the particle suspension 113 and the electrolyte solution 115 flow through passages having a different cross-sectional area, they are adapted to have an identical linear velocity by means of the flow control valves 126, 128.

A computer system 142 for data acquisition related to the change in concentration of the particles over the time change is used in the present invention, which is directly linked to the concentration detector 134.

The inventive device comprises a unit 118 for keeping the diffusion cell 100 at a constant temperature environment, to minimize the influence by temperature during the diffusion process within the diffusion cell 100. The unit 118 may be made of, e.g., a thermal insulation material. The constant temperature environment is acquired by submerging the diffusion cell 100 in a bath with a constant temperature liquid.

It will be understood that various known examples are available for the pressure gauges 130, 132, the flow control valves 128, 136, the reservoirs 122, 124, the connection tubes 120, 152, 158, the suction pumps 138, 140 or the like of the components of the inventive device described above, after having the benefit of this disclosure.

Once the data related to the change in concentration of the particles over the time change is obtained by using the inventive device, the diffusion coefficient can be calculated by employing the mass balance equation disclosed in the previously described researches.

Further, the hindered diffusion coefficient can be calculated in the scheme described hereinbelow from the calculated particle diffusion coefficient.

In principle, on a wall surface of the micropores, Stokes drag force increases due to the hydrodynamic influence and mobility of the particles is reduced by steric exclusion. Concentration partitioning occurs between the region of micropores and that of the bulk due to the steric exclusion between the particles and the wall surface of micropores as well as colloidal interactions as external potentials. The hindered diffusion coefficient H is defined as a ratio of the diffusion coefficient in the micropore $D^p$ to that in the bulk D.

$$H \equiv \frac{D^p}{D_\infty} \qquad \text{Equation 4}$$

Based on Stokes-Einstein equation, the diffusion coefficient in the bulk region D with respect to arbitrary particle concentration C, can be estimated. Using the Boltzmann thermal energy kT, average particle radius $R_p$, solution viscosity $\eta$, and interaction coefficient between the particles $S_2$, the Stokes-Einstein equation is given as follows:

$$D_\infty = \frac{kT}{6\pi\eta R_p}(1 + S_2 C) \qquad \text{Equation 5}$$

The experimental results using the inventive device and method for measuring the particle diffusion coefficient through the micropores of the hollow-fiber will be described below.

Experiment 1

The diffusion cell 100 employed in the experiment 1 is provided with a hollow-fiber having its external diameter 2.2 mm. A space in which the hollow-fiber is mounted has a square cross-section with a width of 4.0 mm and a height of 4.0 mm. The length of the diffusion cell 100 is 10 cm. A silicon rubber packing 14 is used as the sealing member to remove leakage between the upper cell and the lower cell.

Throughout the diffusion through the hollow-fiber, the electrolyte solution may have different values of particle concentration and pH, and these conditions have an influence on the particle diffusion.

First, a strand of a hollow-fiber (manufactured by KOCH Membrane Systems, Inc., MA, U.S.A., Model PM100, internal diameter: 1.1 mm), which has asymmetric micropores and is made of polysulfone for ultrafiltration, is potted with the connection tube 120 to fabricate a module and the module is mounted in the diffusion cell 100 made of transparent acrylic resin and having the dimensions described above. The micropores of PM100 are formed at an inside of the hollow-fiber. An average size of the micropore is about 11.0 nm, surface porosity is about 5.2%, and the wall surface of the micropores is charged.

Next, an electrolyte solution of 1.0 mM concentration and pH 7.0 in which a symmetrical monovalent potassium chloride is dissolved, flows through the outer space 116 of the hollow-fiber by the suction pump and a pressure lower or equal to atmosphere is maintained.

Next, the particle suspension 113 is delivered into the inner space 114 of the hollow-fiber to flow therethrough. Ovalbumin protein selected as the model particle is prolate ellipsoid and is charged on its surface when it is in an aqueous solution. It has a longer axis of 12.1 nm, a shorter axis of 3.3 nm, hydrodynamic equivalent radius of 2.6 nm, and molecular weight of $4.2 \times 10^4$ Daltons.

Next, to allow the fluids flowing through the inner space 114 and the outer space 116 to have the same linear velocity, the flow rates are controlled. Under maintenance of the constant proportions of the pressure difference between inlet and outlet pressures of the electrolyte solution to that between inlet and outlet pressures of the ovalbumin suspension, the ovalbumin is diffused into the electrolyte solution 115 through the micropores 112 of the hollow-fiber 110. The electrolyte solution 115 discharged out of the diffusion cell 100, is immediately passed through the refractive index detector 134. The computer system 142 stores the obtained data and determines the particle concentration by using a previously prepared calibration curve. In order to obtain the accurate mass transfer coefficient and the diffusion coefficient, the change in concentration of the particles is measured for a sufficient time period, i.e., about three hours.

Next, once the change in the particle concentration over the time change (dC/dt) and the particle diffusion coefficient in the bulk region are determined, both the mass transfer coefficient and the particle diffusion coefficient in the pore region are then calculated by applying the mass transfer and the mass transfer resistance relationship, and the hindered diffusion coefficient can finally be obtained.

Figure 4:
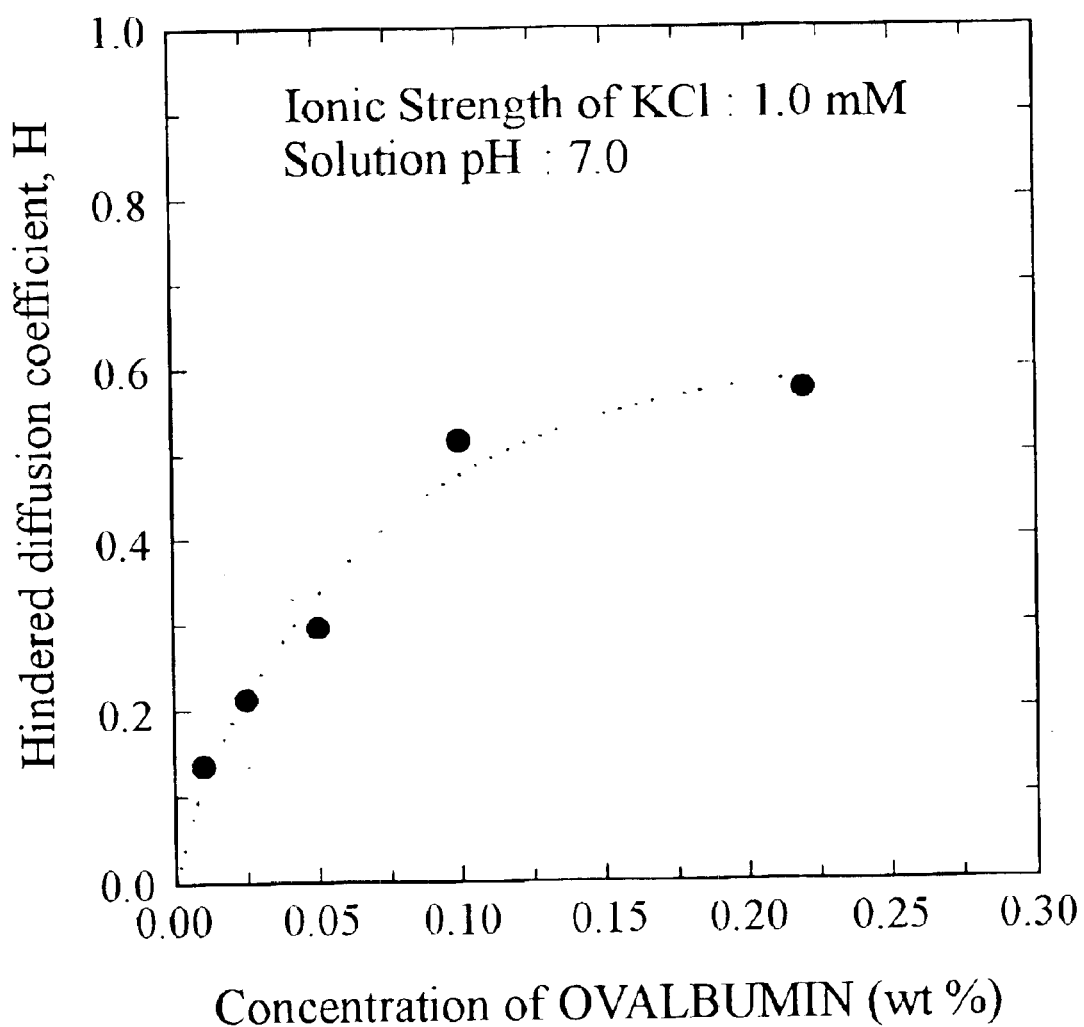
FIG. 4 is a plot of hindered diffusion coefficients obtained from a change in the concentration of ovalbumin protein in a symmetrical monovalent electrolyte solution at constant ionic concentration and constant pH.

From this experiment with respect to the particles and the micropores having dimensions described above, it was established that the hindered diffusion coefficient increases according to the increase of the particle concentration. This is because, as the particle concentration increases, the effect of electrostatic interaction between the particles upon the diffusion becomes dominant rather than that of electrostatic interaction between the particles and the wall surface of the micropores, so that the diffusion from the bulk toward the micropores is more enhanced. The results from this experiment are represented in FIG. 4.

Experiment 2

Figure 5:
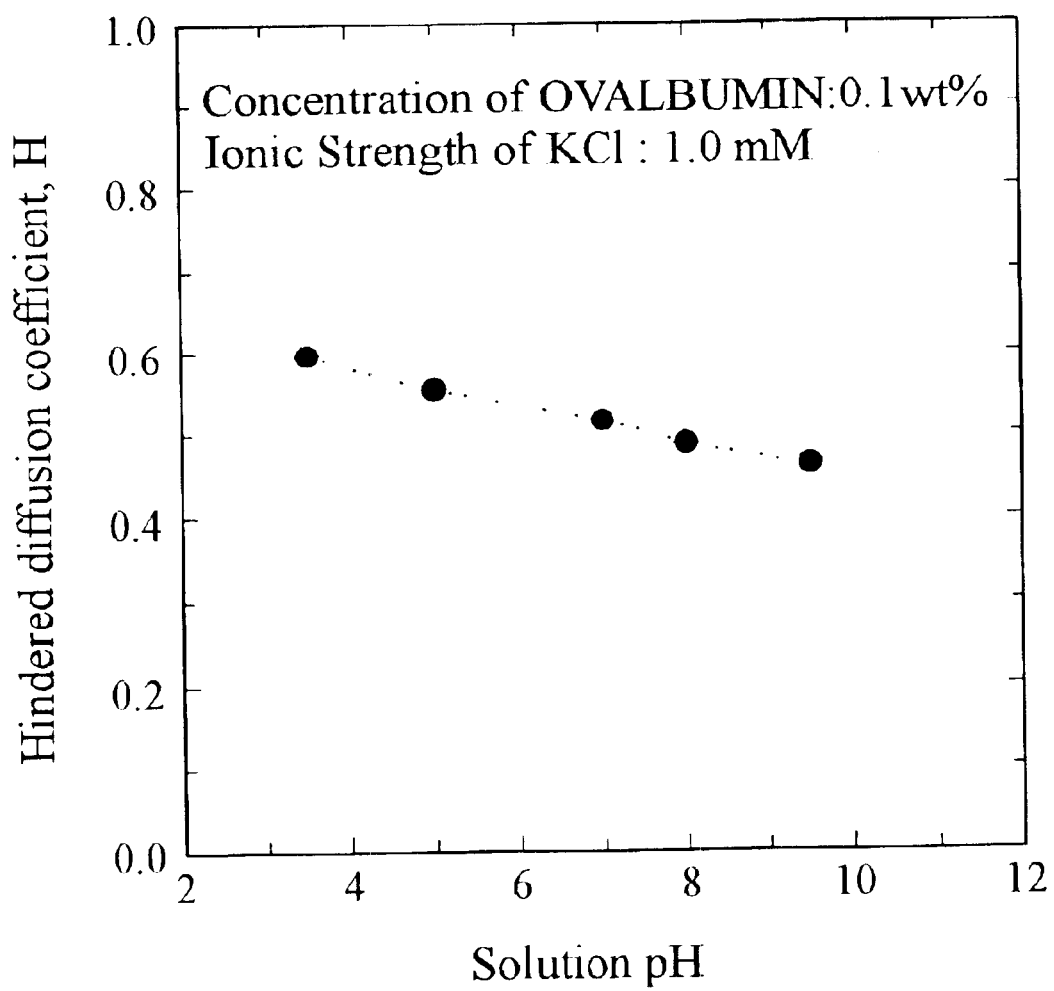
FIG. 5 is a plot of hindered diffusion coefficients with variations of pH for a symmetrical monovalent electrolyte solution at constant ionic concentration and constant ovalbumin concentration.

In this test, the diffusion was carried out with the pH adjusted. The same device as used in Experiment 1 was used. Ovalbumin protein with concentration of 0.1 wt % was used as the model particle, and electrolyte solution with 1.0 mM potassium chloride of symmetrical monovalent electrolyte was also used. The results from this experiment showed that the hindered diffusion coefficient increases with decreasing of pH. This is because the diffusion through the micropores is influenced by the change of the long-range interaction between the particles and the wall surface of the micropores, where both surfaces of particles and micropores exhibit variations of the charge condition depending upon the variations of pH. The results from this experiment are represented in FIG. 5.

As the present invention is configured to measure the change in concentration in a con-current mode such that the particle suspension flows through an inner space of a hollow-fiber while the electrolyte solution flows through an outer space of the hollow-fiber, side-by-side, the measurement may be performed in a short time and the measuring device may be manufactured in compact size.

The inventive device for measuring the particle diffusion coefficient through the micropores of a hollow-fiber can be used for study on the dynamic behavior of particles in confined spaces which requires devices based on micro-scale flow of fluids, examining characteristics of fluid flowing through a microchannel for development of either microfluidics or nanofluidics, and various medical applications especially including hemodialysis.

While the present invention has been shown and described with respect to particular embodiments, it will be apparent to those skilled in the art that many changes and modifications may be made without departing from the spirit and scope of the invention as defined in the appended claims.

What is claimed is:

1. A particle diffusion coefficient measuring device comprising:
    a hollow-fiber comprising a first inlet and a first outlet and micropores on a surface of the hollow-fiber, the hollow-fiber providing a first passage extending from the first inlet to the first outlet for a first fluid having suspended particles to transport through, and the first fluid being introduced into the first passage via the first inlet and being discharged via the first outlet;
    a fluid passage means having a second inlet and a second outlet, formed outside the hollow-fiber to communicate with the inside of the hollow-fiber via the micropores, the fluid passage means providing a second passage for a second fluid to transport through in such a scheme that the second fluid is delivered via the second inlet to flow in the same direction as that of the first fluid and is discharged from the second outlet;
    a concentration change measuring means for detecting a change in concentration of the particles in the second fluid discharged out of the second outlet of the fluid passage means over a time change; and
    a diffusion coefficient calculating means for calculating a particle diffusion coefficient by using the concentration change of the particles over the time change.

2. The particle diffusion coefficient measuring device of claim 1, further comprising a flow rate control means for allowing the first fluid and the second fluid to have the same linear velocity.

3. The particle diffusion coefficient measuring device of claim 1, further comprising a unit for keeping the hollow-fiber and the fluid passage means at a constant temperature.

4. The particle diffusion coefficient measuring device of claim 2, wherein the flow rate control means comprises a first flow control valve for controlling flow rate of the first fluid and a second flow control valve for controlling flow rate of the second fluid.

5. The particle diffusion coefficient measuring device of claim 1, wherein the fluid passage means has a square cross-sectional shape.

6. A method for measuring particle diffusion coefficient comprising the steps of:
   a) introducing a first fluid having suspended particles into an inner space of a hollow-fiber and discharging the first fluid out of the inner space, and introducing a second fluid into a fluid passage formed an outer space of the hollow-fiber in a same direction as that of the first fluid and discharging the second fluid out of the fluid passage, the fluid passage communicating with the inner space of the hollow-fiber;
   b) detecting a change in concentration of the particles in the second fluid being discharged out of the fluid passage over a time change; and
   c) calculating a diffusion coefficient by using the concentration change of the particles over the time change.

7. The method for measuring particle diffusion coefficient of claim 6, wherein the first fluid and the second fluid have the same linear velocity.

8. The method for measuring particle diffusion coefficient of claim 6, wherein the hollow-fiber and the fluid passage are kept at a constant temperature.

9. The particle diffusion coefficient measuring method of claim 6, further comprising the steps of calculating a hindered diffusion coefficient by using the concentration change of the particles over the time change and the particle diffusion coefficient.

* * * * *